(12) United States Patent
Sudhakar et al.

(10) Patent No.: US 6,265,614 B1
(45) Date of Patent: Jul. 24, 2001

(54) OPTICALLY ACTIVE INTERMEDIATES FOR THE PREPARATION OF OPTICALLY ACTIVE SUBSTITUTED OXIMES, HYDRAZONES AND OLEFINS USEFUL AS NEUROKININ ANTAGONISTS

(75) Inventors: Anantha R. Sudhakar, East Brunswick; Suhan Tang, Edison, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/687,905

(22) Filed: Oct. 13, 2000

Related U.S. Application Data

(63) Continuation of application No. 09/168,347, filed on Oct. 8, 1998, now abandoned
(60) Provisional application No. 60/063,632, filed on Oct. 27, 1997.
(51) Int. Cl.$^7$ ................................... C07C 239/00
(52) U.S. Cl. .................. 564/300; 556/420; 556/419; 548/230; 548/540; 560/30; 564/303; 564/304
(58) Field of Search ............... 560/30; 556/420, 556/419; 548/540, 230; 564/300, 303, 304

(56) References Cited

FOREIGN PATENT DOCUMENTS

| WO 9407839A | 4/1994 | (WO) . |
| WO 9528389A | 10/1995 | (WO) . |
| WO 9634857A | 11/1996 | (WO) . |

OTHER PUBLICATIONS

Chemical Abstracts, vol. 106, No. 9, Mar. 2, 1987 Columbus, Ohio, US; abstract No. 66857y, Lu, Matthias C., et al.: "Molecular modification of anticholinergics as probes for muscarinic receptors." p. 569; col. 2; XP 002091113, see abstract Journal of Medicinal Chemistry., vol. 30, No. 2, 1987, pp. 273–278, Washington US.
Chemical Abstracts, vol. 52, No. 2, Jan. 25, 1958 Columbus, Ohio, US; abstract No. 1105f, Lars Westman: "Optical resolution and configuration of alpha–phenylglutaric acid." p. 1105; col. 1; XP002091114, see abstract Arkiv Kemi, vol. 11, 1957, pp. 431–437.
Lu, Matthias C., et al., "Molecular modification of anticholinergics as probes for muscarinic receptors." Journal of Medicinal Chemistry., vol. 30, No. 2, 1987, pp. 273–278, Washington US.

Primary Examiner—Samuel Barts
(74) Attorney, Agent, or Firm—Arthur Mann; William Lee

(57) ABSTRACT

Intermediates having the formula

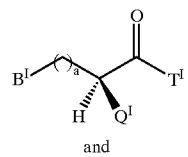

and

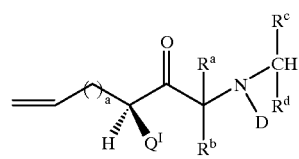

wherein $B^I$ is —$CH_2OH$ or —$CH_2OR^P$, and $R^P$ is an alcohol protecting group;
a is 1, 2, or 3;

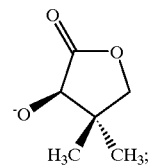

$T^I$ is —OH or
$Q^I$ is phenyl, naphthyl ohr heteroaryl having 1–3 substituents;
$R^a$ and $R^c$ are the same, and are H, or are selected from alkyl, cycloalkyl and aryl groups, the groups being optionally substituted with one or more substituents selected from alkyl cycloalkyl, aryl, or —OH; or $R^a$ and $R^c$ together with the C—N—C chain to which they are bound, form a 5–7 membered ring;
$R^b$ and $R^d$ are the same, and are H, or are selected from alkyl, cycloalkyl and aryl groups, the groups being optionally substituted with one or more substituents selected from alkyl, cycloalkyl, aryl, or —OH; and
D is a directing group capable of directing lithiation alpha to a nitrogen atom of a nitrogen compound having D as a substituent bound to the nitrogen atom when the nitrogen compound is reacted with s-butyl lithium, are disclosed. The intermediates have an enantiomeric excess of the R enantiomer over the corresponding S enantiomer of greater than 85%, preferably, greater than 95%, and are useful for preparing optically active substituted oximes, hydrazones and olefins that are useful as neurokinin antagonists.

5 Claims, No Drawings

OPTICALLY ACTIVE INTERMEDIATES FOR THE PREPARATION OF OPTICALLY ACTIVE SUBSTITUTED OXIMES, HYDRAZONES AND OLEFINS USEFUL AS NEUROKININ ANTAGONISTS

This application is a continuation of U.S. Ser. No. 09/168,347, filed Oct. 8, 1998 now abandoned, which claims the benefit of U.S. Provisional Application No. 60/063,632, filed Oct. 27, 1997.

BACKGROUND OF THE INVENTION

The present invention relates to optically active intermediates, processes for preparing the optically active intermediates, and processes employing the optically active intermediates for preparing optically active substituted oximes, hydrazones and olefins useful as antagonists of tachykinin receptors, in particular as antagonists of the neuropeptides neurokinin-1 receptor ($NK_1$) and/or neurokinin-2 receptor ($NK_2$) and/or neurokinin-3 receptor ($NK_3$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, central nervous system conditions such as migraine and epilepsy, nociception, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma. These $NK_1$ and $NK_2$ receptor antagonists are also useful in the treatment of cough, bronchospasm, inflammatory diseases such as arthritis, central nervous system conditions such as migraine and epilepsy, nociception, and various gastrointestinal disorders such as Crohn's disease.

Substituted oximes, hydrazones and olefins which may be made from the intermediates and processes of the present invention include the oximes, hydrazones and olefins described in International Application No. PCT/US 96/05659, filed on May 1, 1996, the contents of which are fully incorporated herein by reference. It is believed that these compounds exhibit greater activity as neurokinin antagonists when they are in the form of their R-enantiomers. Thus, it is desirable to have intermediates and processes that can be used to make such R-enantiomers. The present invention satisfies this objective.

SUMMARY OF THE INVENTION

The intermediates of the present invention comprise a compound having the formula (1.0)

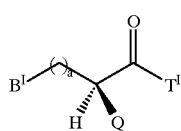

wherein $B^I$ is —$CH_2OH$ or —$CH_2OR^P$, and $R^P$ is an alcohol protecting group;

a is 1, 2, or 3;

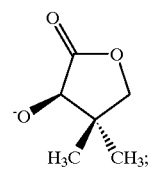

$T^I$ is —OH or

Q is $R^5$-phenyl, $R^5$-naphthyl or $R^5$-heteroaryl;

$R^5$ represents 1–3 substituents independently selected from the group consisting of H, halogeno, —$OR^6$, —$OC(O)R^6$, —$OC(O)N(R^6)(R^7)$, —$N(R^6)(R^7)$, $C_{1-6}$ alkyl, —$C_3$, —$CF_2F_5$, —$COR^6$, —$CO_2R^6$, —$CON(R^6)(R^7)$, —$S(O)_eR^{13}$, —CN, —$OCF_3$, —$NR^6CO_2R^{16}$, —$NR^6COR^7$, —$NR^8CON(R^6)(R^7)$, $R^{15}$-phenyl, $R^{15}$-benzyl, $NO_2$, —$N(R^6)S(O)_2R^{13}$ or —$S(O)_2N(R^6)(R^7)$; or adjacent $R^5$ substituents can form an —O—$CH_2$O— group;

$R^6$, $R^7$, $R^8$, and $R^{13}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of —O—, —S— and —$N(R^{19})$—;

$R^{15}$ is 1 to 3 substituents independently selected from the group consisting of H, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —$C(O)N(R^{10})_2$, —$S(O)_eR^{10a}$, —CN, —$N(R^{10})COR^{10}$, —$N(R^{10})CON(R^{10})_2$ and —$NO_2$;

$R^{16}$ is $C_{1-6}$ alkyl, $R^{15}$-phenyl or $R^{15}$-benzyl;

$R^{10}$ and $R^{10a}$ are independently selected from the group consisting of H and $C_{1-6}$ alkyl;

$R^{19}$ is H, $C_1$–$C_6$ alkyl, —$C(O)N(R^{10})_2$, —$CO_2R^{10}$, —$(C(R^8)(R^9))_f$—$CO_2R^{10}$ or —$(C(R^8)(R^9))_u$—$C(O)N(R^{10})_2$;

$R^9$ is selected from the group consisting of $R^6$ and —$OR^6$;

e is 0, 1 or 2, provided that when e is 1 or 2, $R^{13}$ and $R^{10a}$ are not H;

f is an integer from 1 to 6; and u is an integer from 0 to 6;

said intermediate having an enantiomeric excess of the R enantiomer over the corresponding S enantiomer of greater than 85%.

The intermediates of the present invention also comprise a compound having the formula (2.0)

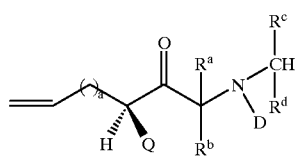

wherein a is 1, 2, or 3;

Q is as defined above;

$R^a$ and $R^c$ are the same, and are H, or are selected from alkyl, cycloalkyl and aryl groups, said groups being optionally substituted with one or more substituents selected from alkyl, cycloalkyl, aryl, or —OH; or $R^a$ and $R^c$ together with the C—N—C chain to which they are bound, form a 5–7 membered ring;

$R^b$ and $R^d$ are the same, and are H, or are selected from alkyl, cycloalkyl and aryl groups, said groups being optionally substituted with one or more substituents selected from alkyl, cycloalkyl, aryl, or —OH; and D is a directing group capable of directing lithiation alpha to a nitrogen atom of a nitrogen compound having D as a substituent bound to the nitrogen atom when said nitrogen compound is reacted with s-butyl lithium, said nitrogen compound having the formula (2.1)

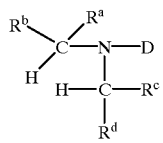

wherein $R^a$, $R^b$, $R^c$, and $R^d$ are as defined above;

said intermediate having an enantiomeric excess of of the R enantiomer over the corresponding S enantiomer of greater than 85%.

The present invention further provides a process for making an optically active R-enantiomer intermediate having the formula:

(3.0)

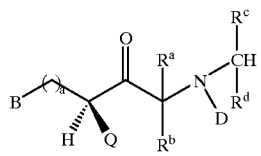

wherein B is —CH=$CH_2$, —$CH_2$OH, or —$CH_2OR^P$, and $R^P$ is an alcohol protecting group;

a is as defined above;

Q is $R^5$-phenyl, $R^5$-naphthyl or $R^5$-heteroaryl;

$R^5$, $R^6$, and $R^7$ are as defined above;

$R^a$, $R^c$, $R^b$ and $R^d$ are as defined above; and

D is a directing group capable of directing lithiation alpha to a nitrogen atom of a nitrogen compound having D as a substituent bound to the nitrogen atom when said nitrogen compound is reacted with s-butyl lithium, said nitrogen compound having the formula

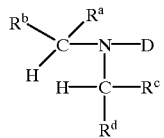

wherein $R^a$, $R^b$, $R^c$, and $R^d$ are as defined above;

said process comprising reacting a compound having the formula

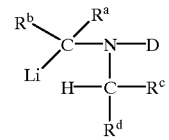

wherein $R^a$, $R^b$, $R^c$, and $R^d$ are as defined above, with a compound having the formula (4.0)

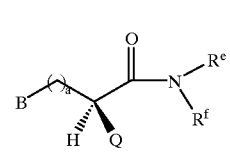

wherein B, a, and Q are as defined above, and $R^e$ and $R^f$ are independently selected from the group consisting of alkyl, alkoxy, cycloalkyl and aryl groups, said groups being optionally substituted with one or more substituents selected from alkyl, alkoxy, cycloalkyl, aryl, $NH_2$, or —OH, or $R^e$ and $R^f$ together with the nitrogen atom to which they are bound, form a 5–7 membered ring.

The present invention further provides a process for making a compound having the formula:

(I)

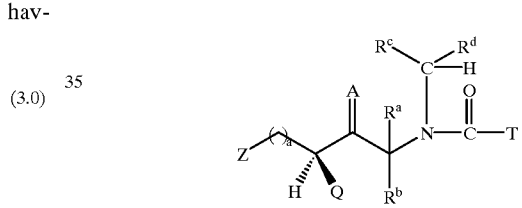

from a compound having the formula (II)

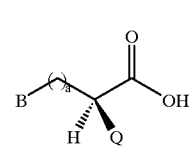

wherein for the formulas above,

B is —CH=$CH_2$, —$CH_2$OH, or —$CH_2OR^P$, and $R^P$ is an alcohol protecting group;

A is =N—$OR^1$, =N—N($R^2$)($R^3$), =C($R^{11}$)($R^{12}$) or =$NR^{25}$;

a is 1,2, or 3;

T is H, $R^4$-aryl, $R^4$-heterocycloalkyl, $R^4$-heteroaryl, phthalimidyl, $R^4$-cycloalkyl or $R^{10}$-bridged cycloalkyl;

Q is $R^5$-phenyl, $R^5$-naphthyl, or $R^5$-heteroaryl;

$R^1$ is H, $C_{1-6}$ alkyl, —(C($R^6$)($R^7$))$_n$—G, —$G^2$, —(C($R^6$)($R^7$))$_p$—M—(C($R^{13}$) ($R^{14}$))$_n$—(C($R^8$)($R^9$))$_u$—G, —C(O)N($R^6$)—(C($R^{13}$) ($R^{14}$))$_n$—(C($R^8$)($R^9$))$_u$—G or —(C($R^6$)($R^7$))$_p$—M—($R^4$-heteroaryl);

$R^2$ and $R^3$ are independently selected from the group consisting of H, $C_{1-6}$ alkyl, —CN, —(C($R^6$)($R^7$))$_n$—G, —$G^2$, —C(O)—(C($R^8$)($R^9$))$_n$—G and —S(O)$_e R^{13}$; or $R^2$ and $R^3$, together with the nitrogen to which they are attached, form a ring of 5 to 6 members, wherein 0, 1 or 2 ring members are selected from the group consisting of —O—, —S— and —N($R^{19}$)—;

$R^4$ and $R^5$ are independently 1–3 substituents independently selected from the group consisting of H, halogeno, —$OR^6$, —$OC(O)R^6$, —$OC(O)N(R^6)(R^7)$, —$N(R^6)(R^7)$, $C_{1-6}$ alkyl, —$CF_3$, —$CF_3F_5$, —$COR^6$, —$CO_2R^6$, —$CON(R^6)(R^7)$, —$S(O)_eR^{13}$, —CN, —$OCF_3$, —$NR^6CO_2R^{16}$, —$NR^6COR^7$, —$NR^8CON(R^6)(R^7)$, $R^{15}$-phenyl, $R^{15}$-benzyl, $NO_2$, —$N(R^6)S(O)_2R^{13}$ or —$S(O)_2N(R^6)(R^7)$; or adjacent $R^4$ substituents or adjacent $R^5$ substituents can form a —O—$CH_2$—O— group; and $R^4$ can also be $R^{15}$-heteroaryl;

$R^6$, $R^7$, $R^8$, $R^{6a}$, $R^{7a}$, $R^{8a}$, $R^{13}$ and $R^{14}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of —O—, —S— and —N($R^{19}$)—;

$R^9$ and $R^{9a}$ are independently selected from the group consisting of $R^6$ and —$OR^6$;

$R^{10}$ and $R^{10a}$ are independently selected from the group consisting of H and $C_{1-6}$ alkyl;

$R^{11}$ and $R^{12}$ are independently selected from the group consisting of H, $C_1$–$C_6$ alkyl, —$CO_2R^6$, —$OR^6$, —$C(O)N(R^6)(R^7)$, $C_1$–$C_6$ hydroxyalkyl, —$(CH_2)_r$—$OC(O)R^6$, —$(CH_2)_r$—$OC(O)CH=CH_2$, —$(CH_2)_r$—O $(CH_2)_s$—$CO_2R^6$, —$(CH_2)_r$—O—$(CH_2)_s$—$C(O)N(R^6)(R^7)$ and —$(CH_2)_r$—$N(R^6)(R^7)$;

$R^{15}$ is 1 to 3 substituents independently selected from the group consisting of H, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —$C(O)N(R^{10})_2$, —$S(O)_eR^{10a}$, —CN, —$N(R^{10})COR^{10}$, —$N(R^{10})CON(R^{10})_2$ and —$NO_2$;

$R^{16}$ is $C_{1-6}$ alkyl, $R^{15}$-phenyl or $R^{15}$-benzyl;

$R^{19}$ is H, $C_1$–$C_6$ alkyl, —$C(O)N(R^{10})_2$, —$CO_2R^{10}$, —$(C(R^8)(R^9))_f$—$CO_2R^{10}$ or —$(C(R^8)(R^9))_u$—$C(O)N(R^{10})_2$;

f, n, p, r and s are independently 1–6;

u is 0–6;

G is selected from the group consisting of H, $R^4$-aryl, $R^4$-hetero-cycloalkyl, $R^4$-heteroaryl, $R^4$-cycloalkyl, —$OR^6$, —$N(R^6)(R^7)$, —$COR^6$, —$CO_2R^6$, —$CON(R^7)(R^9)$, —$S(O)_eR^{13}$, —$NR^6CO_2R^{16}$, —$NR^6COR^7$, —$NR^8CON(R^6)(R^7)$, —$N(R^6)S(O)_2R^{13}$, —$S(O)_2N(R^6)(R^7)$, —$OC(O)R^6$, —$OC(O)N(R^6)(R^7)$, —$C(=NOR^8)N(R^6)(R^7)$, —$C(=NR^{25})N(R^6)(R^7)$, —$N(R^8)C(=NR^{25})N(R^6)(R^7)$, —CN, —$C(O)N(R^6)OR^7$, and —$C(O)N(R^9)$—($R^4$-heteroaryl), provided that when n is 1 and u is 0, or when $R^9$ is —$OR^6$, G is not —OH or —$N(R^6)(R^7)$;

M is selected from the group consisting of a double bond, —O—, —$N(R^6)$—, —$C(O)$—, —$C(R^6)(OR^7)$—, —$C(R^8)(N(R^6)(R^7))$—, —$C(=NOR^6)N(R^7)$—, —$C(N(R^6)(R^7))$=NO—, —$C(=NR^{25})N(R^6)$—, —$C(O)N(R^9)$—, —$N(R^9)C(O)$—, —$C(=S)N(R^9)$—, —$N(R^9)C(=S)$— and —$N(R^6)C(O)N(R^7)$—, provided that when n is 1, G is not OH or —$NH(R^6)$; and when p is 2–6, M can also be —$N(R^6)C(=NR^{25})N(R^7)$— or —$OC(O)N(R^6)$—;

$G^2$ is $R^4$-aryl, $R^4$-heterocycloalkyl, $R^4$-heteroaryl, $R^4$-cycloalkyl, —$COR^6$, —$CO_2R^{16}$, —$S(O)_2N(R^6)(R^7)$ or —$CON(R^6)(R^7)$;

e is 0, 1 or 2, provided that when e is 1 or 2, $R^{13}$ and $R^{10a}$ are not H;

$R^{25}$ is H, $C_1$–$C_6$ alkyl, —CN, $R^{15}$-phenyl or $R^{15}$-benzyl;

Z is

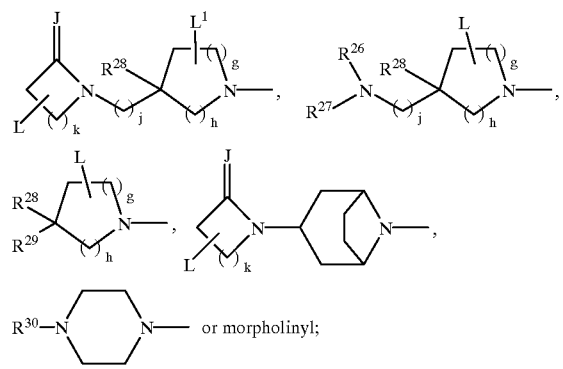

g and j are independently 0–3;

h and k are independently 1–4, provided the sum of h and g is 1–7;

J is two hydrogen atoms, =O, =S, =$NR^9$ or =$NOR^1$;

L and $L^1$ are independently selected from the group consisting of H, $C_1$–$C_6$ alkyl, $C_1$–$C_6$ alkenyl, —$CH_2$-cycloalkyl, $R^{15}$-benzyl, $R^{15}$-heteroaryl, —$C(O)R^6$, —$(CH_2)_m$—$OR^6$, —$(CH_2)_m$—$N(R^6)(R^7)$, —$(CH_2)_m$—$C(O)$—$OR^6$ and —$(CH_2)_m$—$C(O)N(R^6)(R^7)$;

m is 0 to 4, provided that when j is 0, m is 1–4;

$R^{26}$ and $R^{27}$ are independently selected from the group consisting of H, $C_1$–$C_6$ alkyl, $R^4$-aryl and $R^4$-heteroaryl; or $R^{26}$ is H, $C_1$–$C_6$ alkyl, $R^4$-aryl or $R^4$-heteroaryl, and $R^{27}$ is —$C(O)R^6$, —$C(O)$—$N(R^6)(R^7)$, —$C(O)(R^4$-aryl), —$C(O)(R^4$-heteroaryl), —$SO_2R^{13}$ or —$SO_2$—($R^4$-aryl);

$R^{28}$ is H, —$(C(R^6)(R^{19}))_t$—G, —$(C(R^6)(R^7))_v$—$G^2$ or —$NO_2$;

t and v are 0, 1, 2 or 3, provided that when j is 0, t is 1, 2 or 3;

$R^{29}$ is H, $C_1$–$C_6$ alkyl, —$C(R^{10})_2S(O)_eR^6$, $R^4$-phenyl or $R^4$-heteroaryl;

$R^{30}$ is H, $C_1$–$C_6$ alkyl, $R^4$-cycloalkyl, —$(C(R^{10})_2)_w$—($R^4$-phenyl), —$(C(R^{10})_2)_w$—($R^4$-heteroaryl), —$C(O)R^6$, —$C(O)OR^6$, —$C(O)N(R^6)(R^7)$,

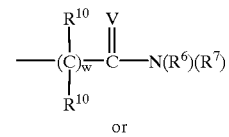

or

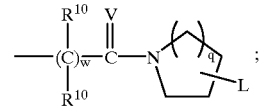

w is 0, 1, 2, or 3;

V is =O, =S or =$NR^6$;

q is 0–4;

$R^a$ and $R^c$ are the same, and are H, or are selected from alkyl, cycloalkyl and aryl groups, said groups being optionally substituted with one or more substituents selected from alkyl, cycloalkyl, aryl, or —OH; or $R^a$ and $R^c$ together with the C—N—C chain to which they are bound, form a 5–7 membered ring;

$R^b$ and $R^d$ are the same, and are H, or are selected from alkyl, cycloalkyl and aryl groups, said groups being optionally substituted with one or more substituents selected from alkyl, cycloalkyl, aryl, or —OH;

said process comprising:
(a) reacting compound II with $NHR^eR^f$ or a salt of $NHR^eR^f$ to form compound III:

(III)

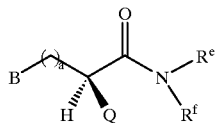

wherein B, a, and Q are as defined above, and $R^e$ and $R^f$ are independently selected from the group consisting of alkyl, alkoxy, cycloalkyl and aryl groups, said groups being optionally substituted with one or more substituents selected from alkyl, alkoxy, cycloalkyl, aryl, $NH_2$, or —OH, or $R^e$ and $R^f$ together with the nitrogen atom to which they are bound, form a 5–7 membered ring;

(b) reacting compound III with

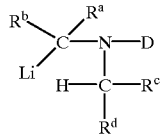

to form compound IV:

(IV)

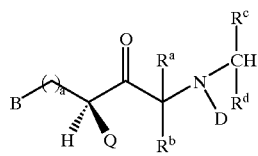

wherein $R^a$, $R^b$, $R^c$, $R^d$, B, a, and Q are as defined above, and D is a directing group capable of directing lithiation alpha to a nitrogen atom of a nitrogen compound having D as a substituent bound to the nitrogen atom when said nitrogen compound is reacted with s-butyl lithium, said nitrogen compound having the formula

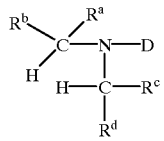

wherein $R^a$, $R^b$, $R^c$, and $R^d$ are as defined above; and carrying out the following steps in any sequence:
(c) (i) reacting compound IV, or the compound obtained from carrying out step (d) and/or step (e), with a compound having the formula $H_2N$—$OR^1$, a salt of $H_2N$—$OR^1$, $H_2N$—$N(R^2)(R^3)$ or $H_2NR^{25}$, wherein $R^1$, $R^2$, $R^3$, and $R^{25}$ are as defined above, to convert the carbonyl group that is bound to the carbon atom having the $R^a$ and $R^b$ substituents

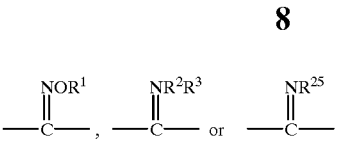

(ii) converting the carbonyl group that is bound to the carbon atom having the $R^a$ and $R^b$ substituents to

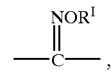

wherein $R^I$ is $C_{1-6}$ alkyl, —$(C(R^6)(R^7))_n$—G, —$G^2$, —$(C(R^6)(R^7))_p$—M—$(C(R^{13})(R^{14}))_n$—$(C(R^8)(R^9))_u$—G, —$C(O)N(R^6)$—$(C(R^{13})(R^{14}))_n$—$(C(R^8)(R^9))_u$—G or —$(C(R^6)(R^7))_p$—M—$(R^4$-heteroaryl), by reacting compound IV, or the compound obtained from carrying out step (d) and/or step (e), with $NH_2OH$ to convert the carbonyl group that is bound to the carbon atom having the $R^a$ and $R^b$ substituents to

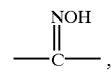

deprotonating the compound obtained after reaction with $NH_2OH$, and reacting the deprotonated compound with $R^IX$, $R^IC(O)Cl$, or $R^IN=C=O$, wherein $R^I$ is as defined above, and X is halogeno; or (iii) reacting compound IV, or the compound obtained from carrying out step (d) and/or step (e), with a phosphorus ylide having $R^{11}$ and $R^{12}$ substituents or a phosphonate carbonation having $R^{11}$ and $R^{12}$ substituents to convert the carbonyl group that is bound to the carbon atom having the $R^a$ and $R^b$ substituents to

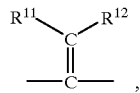

wherein $R^{11}$ and $R^{12}$ are as defined above;
(d) converting the substituent of compound IV, or of the compound obtained from carrying out step (c) and/or step (e), to Z by
(i) if B is —$CH_2OR^P$, deprotecting the alcohol protecting group, followed by oxidation to convert B to H—C(O)—;
(ii) if B is —$CH_2OH$ or —CH=$CH_2$, oxidizing to convert B to H—C(O)—;
(iii) reacting the compound formed in (i) or (ii) with a compound having the formula Z—H, wherein Z is as defined above, to convert the H—C(O)— group formed in (i) or (ii) to Z—$CH_2$—; and
(e) reacting compound IV, or the compound obtained from carrying out step (c) and/or step (d) with an organosilyl halide in the presence of a phenol, and subsequently reacting the compound resulting from the reaction with the organosilyl halide with either $X^I$—C(O)—T in the presence of a base, wherein $X^I$ is halogeno, or with HO(O)C—T, to effect replacement of the D substituent with —C(O)—T, wherein T is as defined above.

For the intermediates and processes described above, Q is preferably R⁵-phenyl, R⁵-naphthyl or R⁵-heteroaryl; an especially preferred definition for Q is R⁵-phenyl. R⁵ is preferably two halogeno substituents.

T is preferably preferably R⁴-aryl, R⁴-heteroaryl, R⁴-cycloalkyl or R¹⁰-bridged cycloalkyl, with R⁴-aryl, especially R⁴-phenyl, being more preferred. R⁴ is preferably two substituents selected from $C_1$–$C_6$ alkyl, halogeno, —$CF_3$ and $C_1$–$C_6$ alkoxy. Preferred definitions for T when T is R⁴-heteroaryl include R⁴-quinolinyl and oxadiazolyl.

A is preferably =N—OR¹ or =N—N(R²)(R³). More preferred are compounds wherein A is =N—OR¹. R¹ is preferably H, alkyl, —(CH₂)$_n$—G, —(CH₂)$_p$—M—(CH₂)$_n$—G or —C(O)N(R⁶)(R⁷), wherein M is —O— or —C(O)N(R⁹)— and G is —CO₂R⁶, —OR⁶, —C(O)N(R⁶)(R⁹), —C(=NOR⁸)N(R⁶)(R⁷), —C(O)N(R⁹)(R⁴-heteroaryl) or R⁴-heteroaryl. R² and R³ are independently preferably H, $C_1$–$C_6$ alkyl, —(C(R⁶)(R⁷))$_n$—G or G².

Preferred definitions of Z are

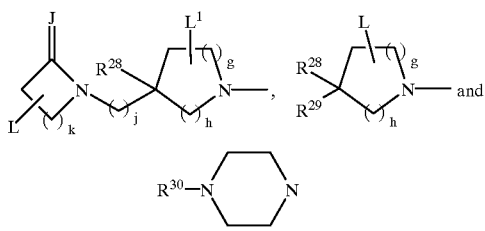

with the following groups being more preferred:

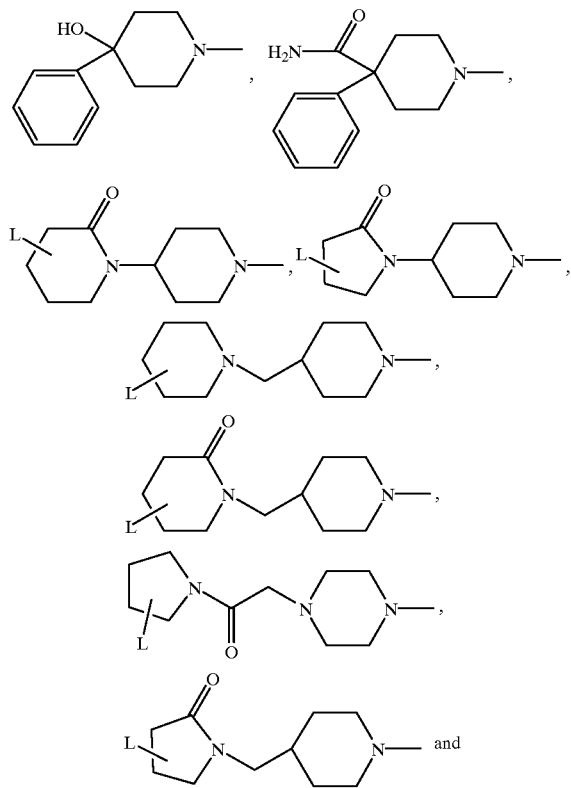

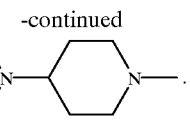

R$^a$, R$^c$, R$^b$, and R$^d$ are preferably selected from H, or lower alkyl, more preferably, methyl. R$^a$, R$^c$, R$^b$, and R$^d$ are most preferably H.

As indicated above, D is a directing group capable of directing lithiation alpha to a nitrogen atom of a compound having the formula shown for compound (2.1). Such directing groups are well known to those skilled in the art of organic synthesis. Typical suitable directing groups include, but are not limited to —C(O)R$^A$, —C(O)—N(R$^A$)(R$^B$), —C(O)—OR$^A$, —CH=NR$^A$, —N=O, —C(=S)R$^A$, and

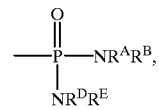

wherein R$^A$, R$^B$, R$^D$, and R$^E$ are independently selected from the group consisting of alkyl, aryl, and cycloalkyl, said groups being optionally substituted by one or more alkyl, aryl, or cycloalkyl groups. An especially preferred directing group is tert-butoxycarbonyl.

R$^e$ and R$^f$ are preferably lower alkyl or lower alkoxy, more preferably, methyl and methoxy, or R$^e$ and R$^f$ together are preferably pyrrolinyl. Especially preferred are processes in which one of R$^e$ and R$^f$ is methoxy, and the other is methyl.

As indicated above, R$^P$ is an alcohol protecting group. Suitable alcohol protecting groups are well known to those skilled in the art of organic synthesis. Typical suitable alcohol protecting groups include, but are not limited to silyl, alkyl, cycloalkyl, aryl, alkoxyalkyl, heterocycloalkyl, and heteroalkyl, optionally substituted with one or more alkyl, cycloalkyl, aryl, alkoxyalkyl, heterocycloalkyl. and heteroalkyl groups. Especially preferred alcohol protecting groups include silyl, benzyl, tetrahydropyranyl, and alkoxymethyl.

DETAILED DESCRIPTION OF THE INVENTION

As used herein, the term "alkyl" means straight or branched alkyl chains having 1–20 carbon atoms, more preferably 1–10 carbon atoms, most preferably, 1–6 carbon atoms. "Lower alkyl" refers to alkyl chains of 1–6 carbon atoms and, similarly, lower alkoxy refers to alkoxy chains of 1–6 carbon atoms.

"Cycloalkyl" means cyclic alkyl groups having 3 to 6 carbon atoms. "Bridged cycloalkyl" refers to $C_7$–$C_{10}$ saturated rings comprised of a cycloalkyl ring or a fused bicycloalkyl ring and an alkylene chain joined at each end to non-adjacent carbon atoms of the ring or rings. Examples of such bridged bicycloalkyl rings are adamantyl, myrtanyl, noradamantyl, norbornyl, bicyclo[2.2.1]heptyl, 6,6-dimethylbicyclo[3.1.1]heptyl, bicyclo[3.2.1]octyl, and bicyclo[2.2.2]octyl.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered saturated rings comprising 1 to 3 heteroatoms independently selected from the group consisting of —O—, —S— and —N(R¹⁹)—, with the remaining ring members being carbon. Examples of heterocycloalkyl rings are tetrahydrofuranyl, pyrrolidinyl, piperidinyl, morpholinyl, thiomorpholinyl and piperazinyl. $R^4$-heterocycloalkyl refers to such groups wherein substitutable ring carbon atoms have an $R^4$ substituent.

"Heteroaryl" refers to 5- to 10-membered single or benzofused aromatic rings comprising 1 to 4 heteroatoms independently selected from the group consisting of —O—, —S— and —N=, provided that the rings do not include adjacent oxygen and/or sulfur atoms. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are indolyl, quinolinyl, thianaphthenyl and benzofurazanyl. N-oxides of nitrogen-containing heteroaryl groups are also included. All positional isomers are contemplated, e.g., 1-pyridyl, 2-pyridyl, 3-pyridyl and 4-pyridyl. $R^4$-heteroaryl refers to such groups wherein substitutable ring carbon atoms have an $R^4$ substituent.

"Silyl" means an organosilyl group.

Where $R^2$ and $R^3$ or $R^6$ and $R^7$ substituents on a nitrogen atom form a ring and additional heteroatoms are present, the rings do not include adjacent oxygen and/or sulfur atoms or three adjacent hetero-atoms. Typical rings so formed are morpholinyl, piperazinyl and piperidinyl.

In the structures in the definition of Z, the substituents L and $L^1$ may be present on any substitutable carbon atom, including in the second structure the carbon to which the —N($R^{26}$)($R^{27}$) group is attached.

In the above definitions, wherein variables $R^6, R^7, R^8, R^9, R^{10}, R^{13}, R^{14}, R^{15}, R^{30}$ and $R^{31}$, for example, are said to be independently selected from a group of substituents, we mean that $R^6, R^7, R^8, R^9, R^{10}, R^{13}, R^{14}, R^{15}, R^{30}$ and $R^{31}$ are independently selected, but also that where an $R^6, R^7, R^8, R^9, R^{10}, R^{13}, R^{14}, R^{15}, R^{30}$ or $R^{31}$ variable occurs more than once in a molecule, those occurrences are independently selected (e.g., if B is =$NR^6$- wherein $R^6$ is hydrogen, X can be —N($R^6$)— wherein $R^6$ is ethyl). Similarly, $R^4$ and $R^5$ can be independently selected from a group of substituents, and where more than one $R^4$ and $R^5$ are present, the substituents are independently selected; those skilled in the art will recognize that the size and nature of the substituent(s) will affect the number of substituents which can be present.

The term "enantiomeric excess" ("e.e.") is used herein to describe a condition in which the amount of the R-enantiomer exceeds the amount of the corresponding S-enantiomer. Depending on the substituents selected, the intermediates of our invention, or the products obtained therefrom, may have more than one chiral center. However, as used herein, references to the R-enantiomer or an e.e. of the R-enantiomer refer to the chiral center at the carbon atom to which substituent Q in the formulas above is bound. When expressed as a percentage, the e.e. represents the percentage obtained by subtracting the amount of the S-enantiomer from the R-enantiomer, and dividing by the sum of the amount of R-enantiomer and S-enantiomer:

e.e. %=100×(R-enantiomer−S-enantiomer)/(R-enantiomer+S-enantiomer). References to "enantiomeric ratio" are intended to mean the ratio of R-enantiomer to the corresponding S-enantiomer. The intermediates of the present invention have an e.e. of at least 85%, preferably at least 95%, more preferably, at least 98%.

Certain substituents, solvents and reagents are referred to herein by the following abbreviations: methyl (Me); ethyl (Et); Ac (acetyl); Bn (benzyl); Bu (butyl); t-Bu (tert-butyl) phenyl (Ph); tert-butoxycarbonyl (Boc); tetrahydrofuran (THF); ethanol (EtOH); methanol (MeOH); t-butyldimethyl silyl (TBS); acetic acid (HOAc); ethyl acetate (EtOAc); N,N-dimethylformamide (DMF); trifluoroacetic acid (TFA); 1-hydroxybenzotriazole (HOBT); diethyl ether ($Et_2O$); 1-(3-dimethylaminopropyl)-3-ethyl carbodiimide (DEC); dicyclohexylcarbodiimide (DCC); lithium hexamethyldisilylamide (LiHMDS); t-butyl methyl ether (TBME); carbonyl di-imidazole ($Im_2CO$); tetramethylenediamine (TMEDA); 2,2,6,6 tetramethyl-1-piperidinoxyl (TEMPO); and trimethyl silyl chloride (TMSCl).

The intermediates comprising a compound having the formula

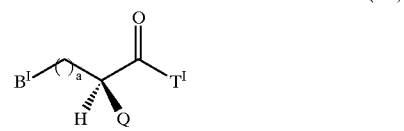

(1.0)

as defined above, can be prepared as shown in the following reaction scheme:

Step A:

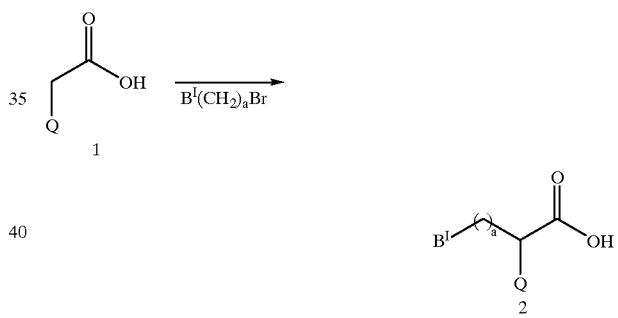

In step A, the carboxylic acid compound 1, wherein $Q^I$ is as defined above, is alkylated by conventional means, e.g., by treating with a suitably strong base (e.g., lithium hexamethyldisilylamide (LiHMDS)) to form an enolate, and reacting the enolate with an alkylating agent, e.g., $B^I(CH_2)_aBr$, wherein $B^I$ and a are as defined above, in a suitable organic solvent, e.g., tetrahydrofuran (THF), at a temperature of from −78 to +50° C., preferably, about −15° C., to form compound 2.

Step B:

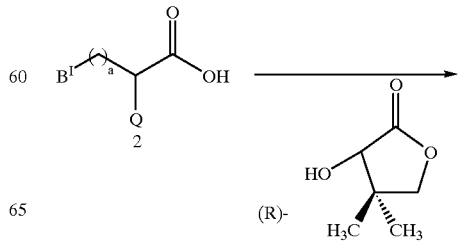

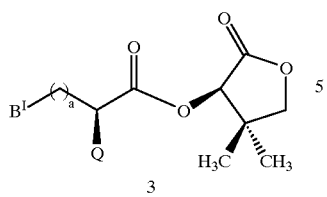

In step B, compound 2 is reacted with a halogenating agent, e.g., $COCl_2$, in the presence of a base, e.g., $Me_2NEt$, to convert compound 2 into an acid halide, preferably an acid chloride, which is subsequently reacted with (R)-pantolactone to form compound 3 in a diastereomeric excess of the RR-diastereomer over the SR-diastereomer of greater than 85%, and usually at least 98%. The formation of the acid halide is carried out in a suitable solvent, e.g., toluene, at a temperature of −78° to +25° C., preferably −15° to 0° C. The reaction of the acid halide with the (R)-pantolactone is carried out in a suitable organic solvent, e.g., toluene, at a temperature of −78° to 0° C., preferably −78° to −50° C. Compound 3 may be recovered from the reaction mixture by conventional means, e.g., by adding water, separating the organic layer, washing it with a solution of $NaHCO_3$, drying over $MgSO_4$, removing the solvent, and purifying the residue by column chromatography.

When $B^I$ is —$CH_2OH$, a suitable alcohol protecting group may be used, i.e., $B^I$ in the reaction scheme above is —$CH_2OR^P$, and the protecting group may be subsequently removed by conventional means to convert the —$CH_2OR^P$ group to —$CH_2OH$.

When $T^I$ is —OH, compound 3 can be hydrolyzed, e.g., by adding water to a solution of compound 3 in a suitable organic solvent, e.g., THF, followed by the addition of $H_2O_2$ and $K_2CO_3$ to form the desired compound. The desired compound may be recovered from the reaction mixture by adding a solution of $Na_2SO_3$ in $H_2O$, extracting the aqueous layer with t-butyl methyl ether (TBME), washing the organic layer with 20% $H_3PO_4$, followed by $H_2O$, and drying over $MgSO_4$. To increase the enantiomeric excess of the product obtained after compound 3 is hydrolyzed, the product can be dissolved in a mixture of TBME and THF (4 parts TBME, 1 part THF), followed by the addition of t-$BuNH_2$, which can then be heated, cooled and filtered to give the ammonium salt. This procedure can be repeated several times until a sufficiently high enantiomeric ratio is obtained. The ammonium salt can then be added to a solution of TBME and 50% aqueous $H_3PO_4$, after which the organic layer can be separated, washed with brine, and dried over $MgSO_4$ to give the pure carboxylic acid compound (1.0), wherein $T^I$ is —OH, with an e.e. of the R-enantiomer over the S-enantiomer of at least 98%.

Intermediates comprising compounds having the formula

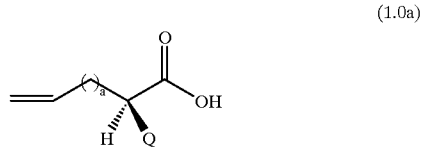

(1.0a)

wherein Q and a are as defined above, can be prepared as shown in the following reaction scheme:

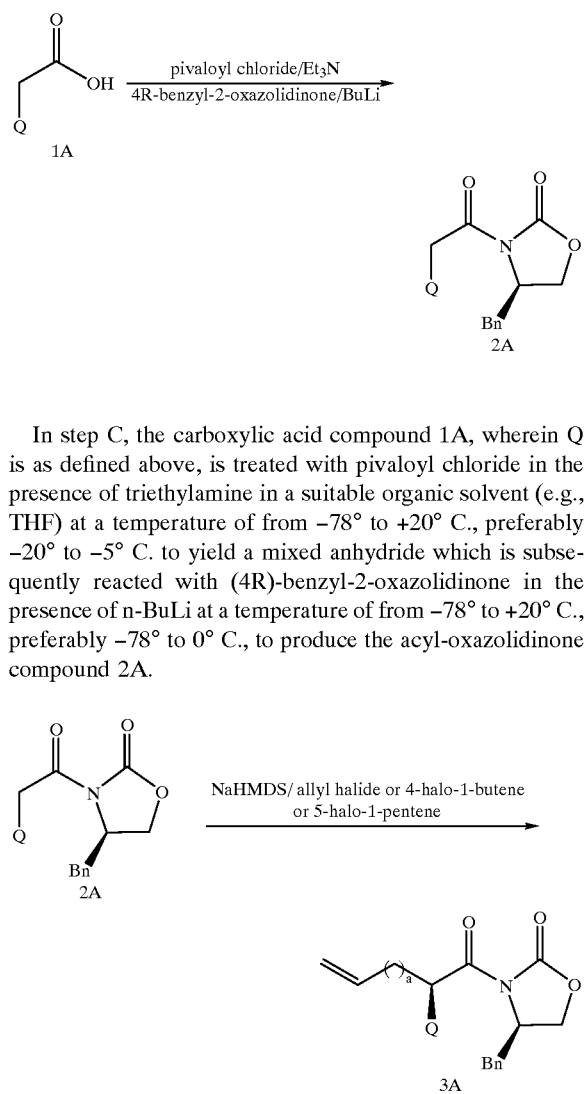

In step C, the carboxylic acid compound 1A, wherein Q is as defined above, is treated with pivaloyl chloride in the presence of triethylamine in a suitable organic solvent (e.g., THF) at a temperature of from −78° to +20° C., preferably −20° to −5° C. to yield a mixed anhydride which is subsequently reacted with (4R)-benzyl-2-oxazolidinone in the presence of n-BuLi at a temperature of from −78° to +20° C., preferably −78° to 0° C., to produce the acyl-oxazolidinone compound 2A.

In step D, compound 2A is deprotonated with a strong base, preferably sodium bis(trimethylsilyl)amide (NaHMDS) in a suitable organic solvent (e.g., THF) at a temperature of from −78° to 0° C., preferably, −78° to −50° C., and then alkylated with an allyl halide (e.g., allyl iodide), a 4-halo-1-butene (e.g., 4-bromo-1-butene), or a 5-halo-1-pentene (e.g., 5-bromo-1-pentene) at a temperature of from −78° to +20° C., preferably −78° to −60° C. to produce compound 3A.

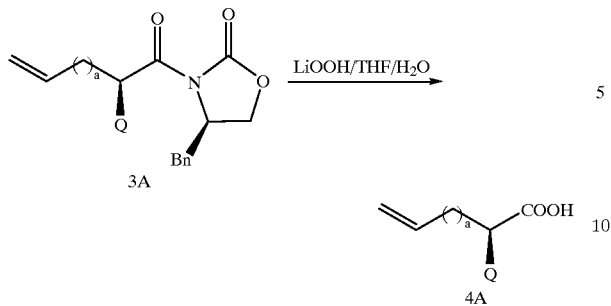

3A

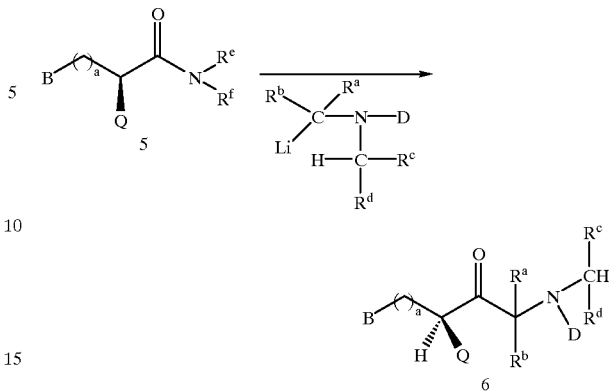

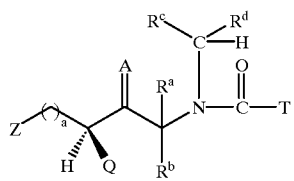

4A

In step E, the oxazolidinone, 3A, is hydrolyzed with lithium hydrogen peroxide to produce the carboxylic acid, 4A. The hydrolysis is preferably carried out by forming a solution of the oxazolidinone compound 3A in a mixture of THF/H$_2$O, and adding hydrogen peroxide and lithium hydroxide monohydrate thereto at a temperature of from −20° to +20° C., preferably from −5° to 0° C.

Compound (1.0) wherein T' is —OH or Compound (1.0 a) can be used to prepare compounds having the formula:

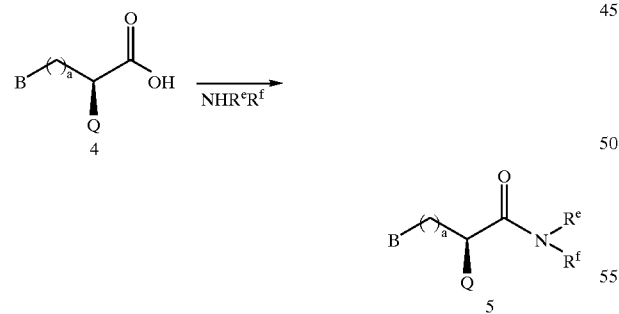

as shown in the following reaction scheme, wherein Z, a, Q, A, R$^a$, R$^b$, R$^c$, R$^d$ and T are as defined above, and B represents —CH=CH$_2$, —CH$_2$OH, or —CH$_2$OR$^P$, and R$^P$ is an alcohol protecting group:

Step 1:

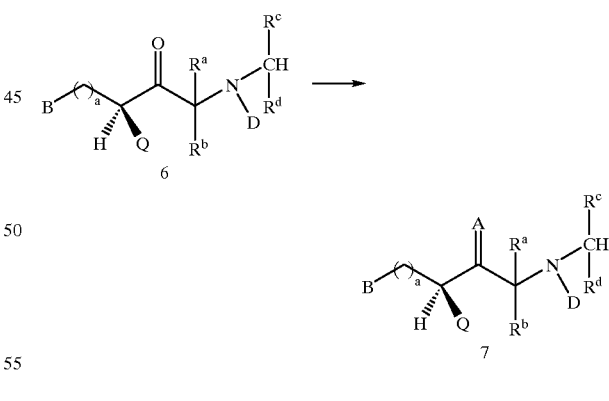

In step 1, the carboxylic acid compound 4 (representing compound (1.0) wherein T' is —OH or compound (1.0 a)) is converted to compound 5 using standard methods, e.g., by reacting it with a compound having the formula NHR$^e$R$^f$, optionally in the form of a salt, in the presence of a coupling agent, e.g., carbonyl di-imidazole (Im$_2$CO), DCC, or DEC in a suitable organic solvent, e.g., CH$_2$Cl$_2$ at a temperature of from 0° C. to 50° C.

In step 2, compound 5 is reacted with the lithium compound shown above, wherein D, R$^a$, R$^b$, R$^c$, and R$^d$ are as defined above, to form compound 6. This reaction is carried out in a suitable organic solvent, e.g., THF or t-butylmethyl ether (TBME), at a temperature of from −78° to −20° C., preferably −78° to −50° C. The reaction may be quenched, if necessary, by transferring into a solution of acetic acid in an organic solvent. Compound 6 may be recovered by conventional means, e.g., by washing with water, an aqueous NaHCO$_3$ solution, drying over MgSO$_4$, and removing the solvents by column chromatography. The lithium compound may be prepared by conventional means, e.g., by reacting s-Bu-Li with the amide N(D)(CHR$^a$R$^b$)(CHR$^c$R$^d$) in an organic solvent, e.g., TBME, at a temperature of from −78° to −20° C., preferably −78° to −50° C., and preferably in the presence of a tertiary amine, e.g., tetramethylenediamine (TMEDA) to accelerate lithiation. The lithium compound prepared in this fashion generally does not need to be recovered from the reaction medium, i.e., compound 5 may be added directly to the reaction medium of the resulting lithium compound.

In step 3, compound 6 is converted to compound 7, wherein A is as defined above, by one of the following procedures. When A is =N—OR$^1$, =N—N(R$^2$)(R$^3$), or =NR$^{25}$, compound 6 is converted to compound 7 by reacting compound 6 with a compound selected from H$_2$N—OR$^1$, H$_2$N—N(R$^2$)(R$^3$) or H$_2$NR$^{25}$, or a salt thereof, e.g., the HCl salt, in a suitable organic solvent, e.g., pyridine, CH$_3$OH, or CH$_3$CH$_2$OH, at a temperature of 0° to 100° C., preferably 50° to 70° C. Alternatively, compound 7, wherein A is =NOR$^1$ and R$^1$ is not H can be prepared by first forming a compound wherein A is =NOH according to the procedure described above, deprotonating with a suitable base, e.g., NaH or $Cs_2CO_3$, and subsequently treating with an electrophile having the $R^1$ substituent, e.g., an alkyl halide ($R^1$-halogen), an acid chloride ($R^1C(O)Cl$), or an isocyanate ($R^1$—N=C=O). When A is =$CR^{11}R^{12}$, compound 6 is converted to compound 7 by treating compound 6 with a phosphorus ylide having substituents $R^{11}$ and $R^{12}$, e.g., $Ph_3P$=$CHR^{11}R^{12}$, or a phosphonate carbonation having $R^{11}$ and $R^{12}$ substituents, e.g., $(EtO)_2P(O)C^{(-)}HR^{11}R^{12}$ in a suitable organic solvent, e.g., THF or ether, preferably ether, at a temperature of from -15° to 65° C. The phosphorus ylides may be prepared by deprotonation of phosphonium salts, e.g., phosphonium halides with a strong base. Similarly, the phosphonate carbanions may be generated by treating phosphonate esters with a strong base.

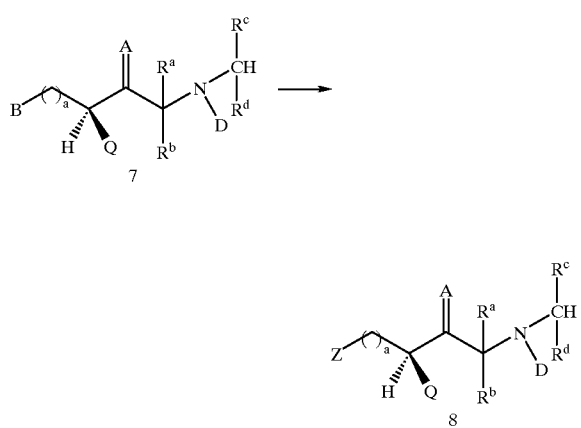

7

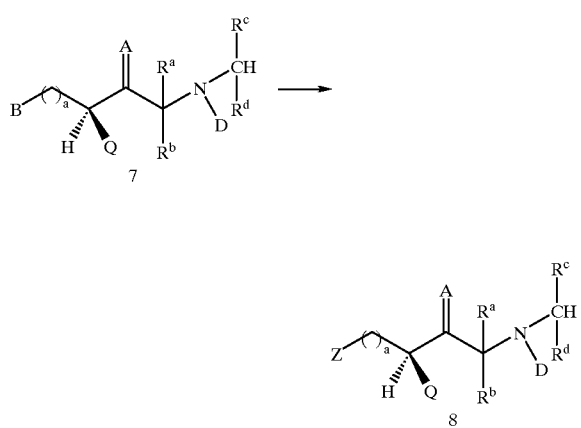

8

In step 4, compound 7 is oxidized to convert the B substituent to H—C(O)—, and reacted with a compound having the formula Z—H, wherein Z is as defined above. The reaction with Z—H may be carried out with compound 7 in the form of a free base or as its acid salt, e.g., HCl or maleate, preferably with a hydride source such as $NaBH_3CN$ or sodium triacetoxyborohydride in a suitable organic solvent, preferably THF, optionally with 3A sieves to obtain compound 8. Any suitable temperature can be used with preferable temperatures between 0° C. and 25° C. When B is —$CH_2OH$, the oxidation may be carried out with any suitable oxidizing agent (e.g., sodium hypochlorite in the presence of TEMPO, pyridinium chlorochromate, chromium trioxide-pyridine, pyridinium dichromate, oxalyl chloride-dimethylsulfoxide, acetic anhydride-dimethylsulfoxide, or periodinane, most preferably, sodium hypochlorite in the presence of TEMPO) in an inert solvent, e.g., chlorinated hydrocarbons (e.g. $CH_2Cl_2$, 1,2-dichloroethane, or $CHCl_3$). Any suitable temperature can be used with preferable temperatures between -78° C. and 25° C. When B is —$CH_2OR^P$, the alcohol protecting group, $R^P$, may be removed, i.e., compound 7 may be deprotected, prior to the oxidation by conventional means. When $R^P$ is a silyl protecting group, removal of the protecting group is preferably carried out with a fluoride source such as HF in $CH_3CN$ or tetrabutyl-ammonium fluoride in an inert solvent such as an ether. This step can also be carried out with acid (e.g. HOAc, $CF_3CO_2H$, p-toluene sulfonic acid, $H_2SO_4$, or HCl) and water in an inert solvent such as an ether, or in a chlorinated hydrocarbon (e.g. $CH_2Cl_2$, 1,2-dichloroethane, or $CHCl_3$). Any suitable temperature can be used, preferably temperatures between 0° C. and 80° C. When B is —CH=$CH_2$, the oxidative cleavage of the double bond may be carried out with any suitable oxidizing agent, e.g., permaganate ion in solution with periodate ion, $OsO_4$ or $RuO_4$ in combination with $NaIO_4$, Cr(VI) oxidizing reagents, or ozone. Preferably, ozone is used for the oxidative cleavage. The ozonolysis may be carried out in an organic solvent, preferably EtOAc. or ethanol at any suitable temperature, preferably -78 to 0° C.

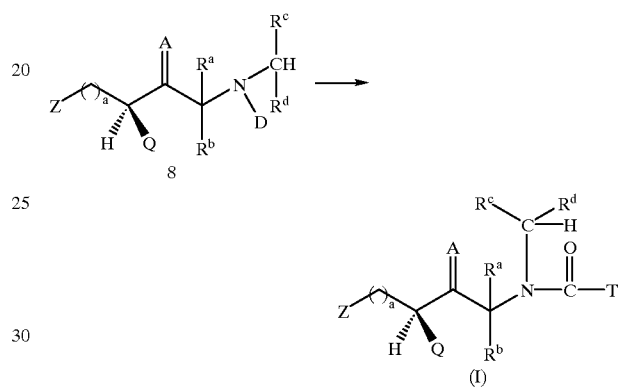

8

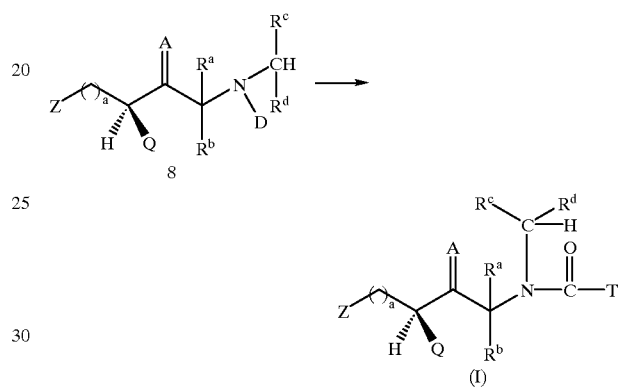

(I)

In step 5, compound 8 is converted to compound (I) by reacting it with an organosilyl halide (e.g., trimethyl silyl chloride (TMSCl)) in the presence of a phenol to displace the D substituent, and subsequently reacting the product obtained from the reaction with the organosilyl halide with a carboxylic acid having the formula HO(O)C—T, wherein T is as defined above. The acylation is preferably carried out with the carboxylic acid in the presence of a dehydrating agent, e.g., DEC in the presence of HOBT, at temperatures of from 0° to 50° C., preferably 0° to 25° C. The reaction with the organosilyl halide may be carried out in any suitable organic solvent, e.g., methylene chloride, at temperatures of from 0° to 50° C., preferably 0° to 25° C. Alternatively, the acylation of the product obtained from the reaction with the organosilyl halide may be achieved by reacting it with an acid halide having the formula $X^I$—C(O)—T, where $X^I$ is halogeno and T is as defined above, in the presence of a base, preferably a tertiary alkyl amine, at temperatures from -50° to +25° C.

Steps 3, 4, and 5 may be carried out in any sequence. For example, compound 6 from step 2 may be subjected to step 5 first, and the resulting product subjected to step 4, followed by step 3. Preferably, steps 3, 4, and 5 are carried out in the sequence shown above.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \NH | \NCOalkyl, \NCObenzyl, \NCOphenyl, |
| | \NCH₂OCH₂CH₂Si(CH₃)₃, \NC(O)OC(CH₃)₃, |
| | \N-benzyl, \NSi(CH₃)₃, \NSi(CH₃)₂—C(CH₃)₃ |
| —NH₂ | (succinimide structure) |
| —OH | —OCH₃, —OCH₂OCH₃, —OSi(CH₃)₃, —OSi(CH₃)₂—C(CH₃)₃, or —OCH₂phenyl |

The following examples are intended to illustrate the the invention, but should not be construed to limit the scope of the disclosure.

EXAMPLE 1

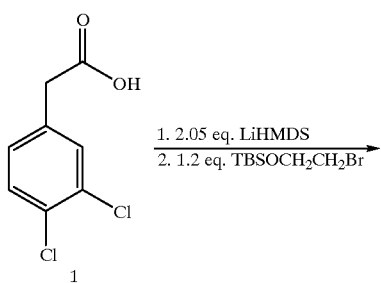

1. 2.05 eq. LiHMDS
2. 1.2 eq. TBSOCH₂CH₂Br

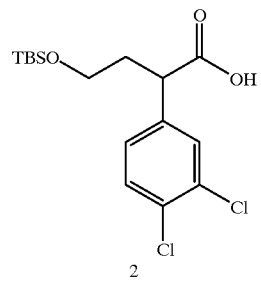

2

To a solution of LiHMDS (1.0 M in THF, 1.05 L, 1.05 mol) at −15° C., a solution of 3,4-dichlorobenzoic acid 1, obtained from Lancaster Synthesis, Inc. (104.5 g, 0.51 mol) in 300 mL THF was added. The resulting solution was stirred at 0° C. for 1 hour. After re-cooling to −15° C., TBSOCH₂CH₂Br (146.3 g, 0.61 mol) was added. The solution was stirred at −15° C. for 16 hours, then was poured into 1.2 L of H₂O. After adding 200 mL of EtOH, the aqueous solution was extracted with 800 mL of TBME. The aqueous layer was acidified to a pH=3–4 with H₃PO₄, and then was extracted with TBME (1.5 L). The organic layer was dried over MgSO₄. Removal of solvent followed by crystallization from 500 mL of heptane gave the pure product 2 (136.5 g, 78% yield) as a white solid.

$^1$H NMR (400 Mhz, CDCl₃): δ 0.02 (s, 6H), 0.85 (s, 9H), 1.85 (m, 1H), 2.34 (m, 1H), 3.45 (m, 1H), 3.63 (m, 1H), 3.79 (m, 1H), 7.10 (m, 1H), 7.38 (m, 2H).

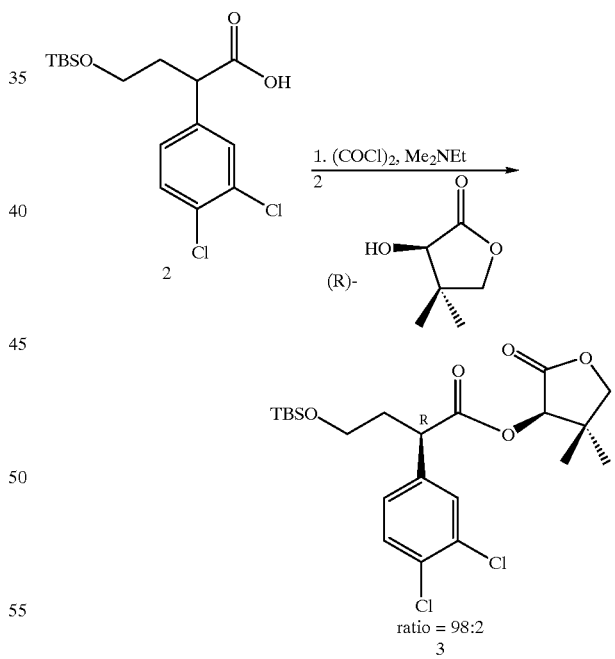

ratio = 98:2
3

To a solution of acid 2 (81.5 g, 0.22 mol) and Me₂NEt (121.4 mL, 1.12mol) in 1.1 L of toluene at 0° C., (COCl)₂ (21.5 mL, 0.247 mol) was added. The mixture was stirred at 0° C. for 1 hour, then was warmed to room temperature and stirred for 3 hours. After re-cooling to −55° C., (R)-pantolactone (35 g, 0.27 mol) was added. The mixture was stirred at −55° C. for 16 hours, and then was diluted with 500 mL of H₂O. The organic layer was separated, and was washed with 500 mL of saturated NaHCO₃ solution. After drying over MgSO₄, the solvent was removed and the residue was purified via column chromatography (silica gel, 30% TBME/heptane) to give the product 3 (87.3 g, 82% yield) as a mixture of (RR) and (RS) diastereomers in a ratio of the RR-diastereomer to the SR-diastereomer of 98:2.

¹H NMR (400 Mhz, CDCl₃): δ 0.05 (s, 6H), 0.85 (s, 9H), 1.08 (s, 3H), 1.19 (s, 3H), 1.98 (m, 1H), 2.30 (m, 1H), 3.48 (m, 1H), 3.61 (m, 1H), 4.00 (m, 3H), 5.34 (s, 1H), 7.18 (m, 1H), 7.40 (m, 2H).

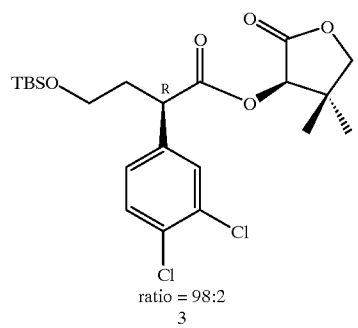

ratio = 98:2
3

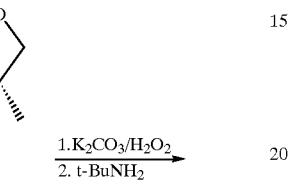

1. K₂CO₃/H₂O₂
2. t-BuNH₂

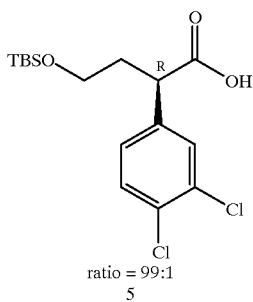

ratio = 99:1
5

To a solution of ester 3 (218.0 g, 0.46 mol) in 2L of THF and 500 mL of H₂O at −5° C. was added H₂O₂ (30%, 416 g, 3.68 mol), followed by K₂CO₃ (254 g, 1.84 mol). The resulting mixture was stirred at −5° C. for 16 hours. Then a solution of Na₂SO₃ (500 g) in 1L of H₂O was added. The aqueous layer was extracted with 2L of TBME. The organic layer was washed with 500 mL of 20% H₃PO₄ followed by 500 mL of H₂O, and was dried over MgSO₄. Removal of the solvent gave the crude acid as a solid. Chiral HPLC indicated an enantiomeric ratio of 88:12.

The above crude solid was then dissolved in 2.5 L of TBME/THF (4:1 v/v) at room temperature. t-BuNH₂ (36.7 g, 0.5 mol) was then added. The mixture was heated to reflux untill all the solid was dissolved. Then the solution was allowed to slowly cool to room temperature. The solid was filtered off to give the ammonium salt as an enantiomeric ratio of 94.4:5.6. This crystallization was repeated four times to give a salt which had an enantiomeric ratio of 99:1. The salt was then added to a solution of TBME (1 L) and 50% aqueous H₃PO₄ (500 mL). The organic layer was separated, washed with brine, dried over MgSO₄. Removal of solvent gave the pure acid 5 as an enantiomeric ratio of 99:1.

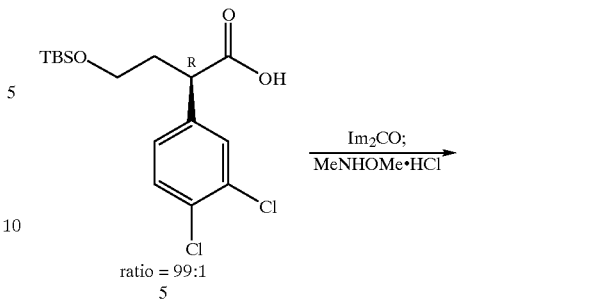

ratio = 99:1
5

Im₂CO;
MeNHOMe·HCl

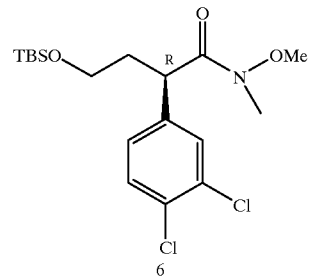

6

To a mixture of Im₂CO (44.6 g, 0.276 mol) in 100 mL of CH₂Cl₂ at 0° C., a solution of acid 5 (100 g, 0.276 mol) in 300 mL of CH₂Cl₂ was added slowly. The resulting solution was then stirred at 0° C. for 1 hour. A mixture of MeNHO-Me·HCl (40 g, .41 mol) in 300 mL of CH₂Cl₂ was added. The mixture was stirred at 0° C. for 16 hours, and 600 mL of 2N HCl was added followed by 2L of heptane. The organic layer was separated, washed by 20% K₂CO₃ aqueous solution (500 mL), and was dried over MgSO₄. Removal of the solvent then gave the desired product 6 (110 g) as an oil, which was used without further purification. The enantiomeric ratio was 99:1.

1H NMR (400Mhz, CDCl₃): δ 0.02 (s, 6H), 0.90 (s, 9H), 1.85 (m, 1H), 2.25 (m, 1H), 3.15 (s, 3H), 3.44 (m, 1H), 3.53 (m, 1H), 3.55 (s, 3H), 4.27 (m, 1H), 7.15 (m, 1H), 7.40 (m, 2H).

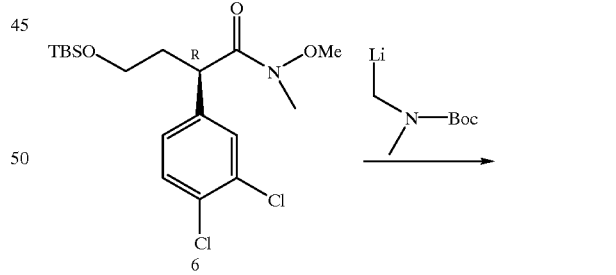

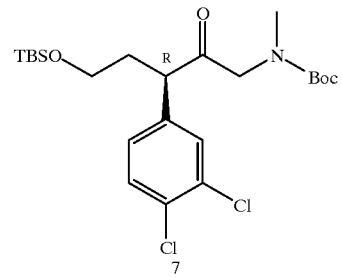

7

To a solution of N-Boc-dimethylamine (50 g, 344 mmol) in 400 mL of TBME, TMEDA (52 mL, 344 mmol) was added. The solution was cooled to −78° C. and s-BuLi (1.3M in cyclohexane, 298 mL, 387 mmol) was added. The resulting mixture was stirred at −78° C. for 1 hour. A solution of amide 6 (34.9 g, 86 mmol) in 100 mL of THF was added. After stirring at −78° C. for 0.5 hours, the reaction was quenched by transfering into a solution of HOAc (98 mL) in 100 mL of MeOH and 400 mL of THF at −78° C. The organic solution was then washed with H₂O, aq. NaHCO₃ solution, and was dried over MgSO₄. Removal of solvents followed by column chromatography (silica gel, 15% TBME/heptane) gave the pure product 7 (40 g, 95% yield) as a colorless oil, with an enantiomeric ratio of 99:1.

$^1$H NMR (400 Mhz, CDCl$_3$): δ 0.07 (s, 6H), 0.85 (s, 9H), 1.24 (s, 9H), 1.81 (m, 1H), 2.20 (m, 1H), 2.79 (s, 3H), 3.31 (m, 1H), 3.54 (m, 1H), 3.83–4.19 (m, 3H), 7.00–7.43 (m, 3H).

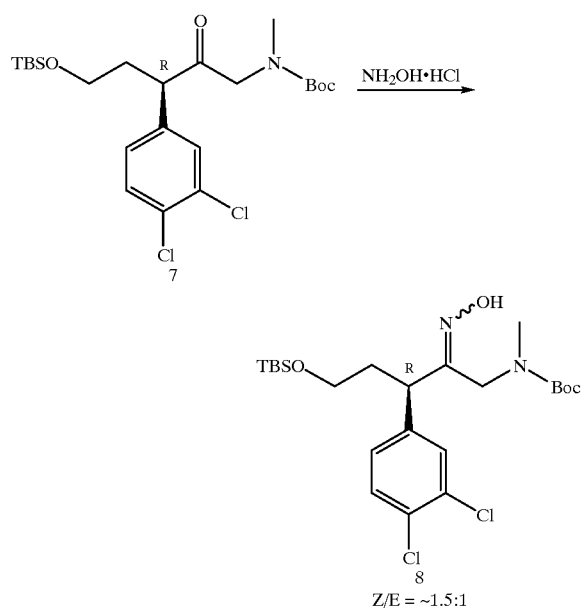

To a solution of ketone 7 (25.5 g, 52 mmol) in 150 mL of pyridine, NH₂OH.HCl (7 g, 101.2 mmol) was added. The solution was heated to 50–55° C. for 7 hours. After cooling to room temperature, the reaction was diluted with 100 mL of TBME. The organic solution was washed with H₂O, aq. NaHCO₃ solution, and was dried over MgSO₄. Removal of solvents followed by column chromatography (silica gel, 15% EtOAc/heptane) gave 16.1 g of Z-oxime 8 and 10.1 g of E-oxime 8 (100% combined yield) as a colorless oil, with an enantiomeric ratio greater than 97:3.

Z-isomer: $^1$H NMR (400 Mhz, CDCl$_3$): δ 0.01 (s, 6H), 0.89 (s, 9H), 1.45 (s, 9H), 1.78 (m, 1H), 2.18 (m, 1H), 2.56 (s, 3H), 3.29 (m, 1H), 3.55 (m, 1H), 3.77 (m, 1H), 3.96 (m, 1H), 4.27 (m, 1H), 7.06 (m, 1H), 7.35 (m, 2H), 8.34 (br, 1H).

E-isomer: $^1$H NMR (400 Mhz, CDCl$_3$): δ 0.00 (s, 6H), 0.84 (s, 9H), 1.40 (s, 9H), 2.08–2.35 (m, 2H), 2.56 (s, 3H), 3.55 (m, 2H), 3.78–4.15 (m, 2H), 4.58 (m, 1H), 7.16 (m, 1H), 7.35 (m, 2H), 8.45 (br, 1H).

Oxime 8 is a useful intermediate that can be used to prepare optically active compounds of formula (I) via the procedures set forth in steps 4 and 5, above.

EXAMPLE 2

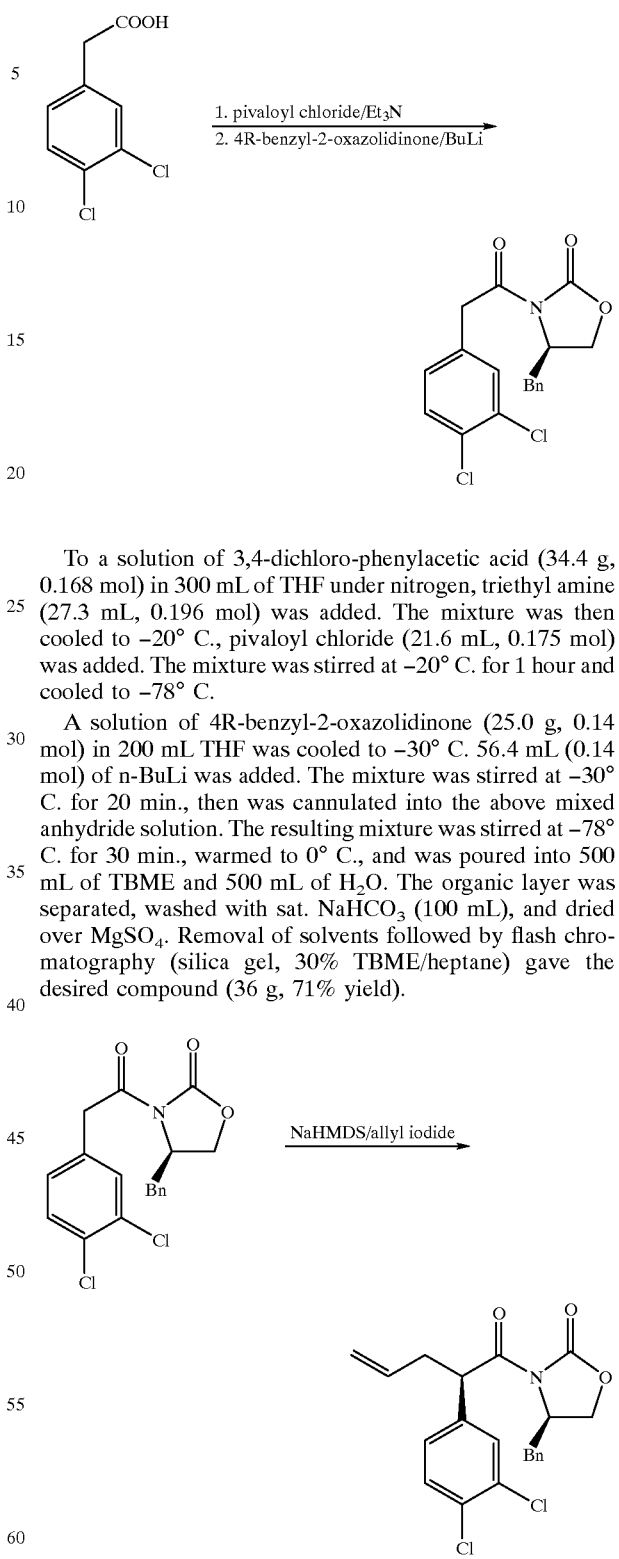

To a solution of 3,4-dichloro-phenylacetic acid (34.4 g, 0.168 mol) in 300 mL of THF under nitrogen, triethyl amine (27.3 mL, 0.196 mol) was added. The mixture was then cooled to −20° C., pivaloyl chloride (21.6 mL, 0.175 mol) was added. The mixture was stirred at −20° C. for 1 hour and cooled to −78° C.

A solution of 4R-benzyl-2-oxazolidinone (25.0 g, 0.14 mol) in 200 mL THF was cooled to −30° C. 56.4 mL (0.14 mol) of n-BuLi was added. The mixture was stirred at −30° C. for 20 min., then was cannulated into the above mixed anhydride solution. The resulting mixture was stirred at −78° C. for 30 min., warmed to 0° C., and was poured into 500 mL of TBME and 500 mL of H₂O. The organic layer was separated, washed with sat. NaHCO₃ (100 mL), and dried over MgSO₄. Removal of solvents followed by flash chromatography (silica gel, 30% TBME/heptane) gave the desired compound (36 g, 71% yield).

To a solution of the starting oxazolidinone (36 g, 0.099 mol) in 100 mL THF at −78° C. under nitrogen, 124 mL of NaHMDS as 1.0 M solution in THF (0.124 mol) was added. After stirring at −78° C. for 30 min., 30 mL of allyl iodide (0.3 mol) was added. The resulting solution was stirred at −78° C. for 1 hour, then was quenched by pouring into 500 mL of TBME and 500 mL of H₂O. The organic layer was separated, washed with sat. NaCl (100 mL), and dried over MgSO₄. Removal of solvents followed by flash chromatography (silica gel, 5% TBME/heptane) gave the desired allyl oxazolidinone (24 g, 60% yield) as an oil.

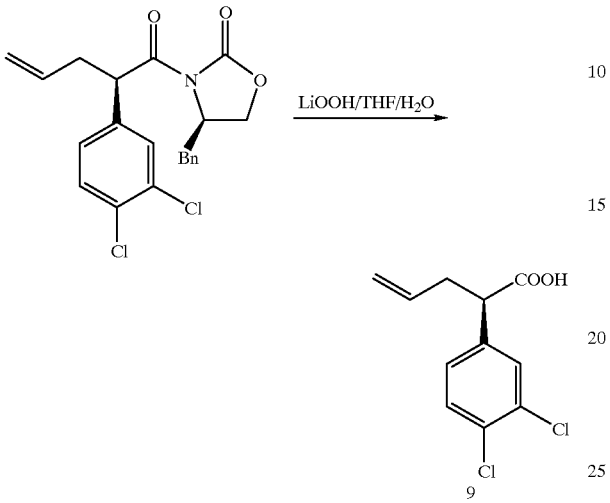

To a solution of the allyl oxazolidinone (18 g, 44.6 mmol) in 600 mL of 4:1 v/v THF/H₂O at 0° C., 41 mL of 30% H₂O₂ (356 mmol) was added, followed by 7.5 g of LiOH.H₂O (178 mmol). The resulting solution was stirred at 0° C. for 30 min., then was quenched by adding 20 g of sodium sulfite, and poured into 500 mL of EtOAc and 500 mL of H₂O. The organic layer was separated, and dried over MgSO₄. Removal of solvents gave the desired chiral acid 9 (9.8 g, 90% yield).

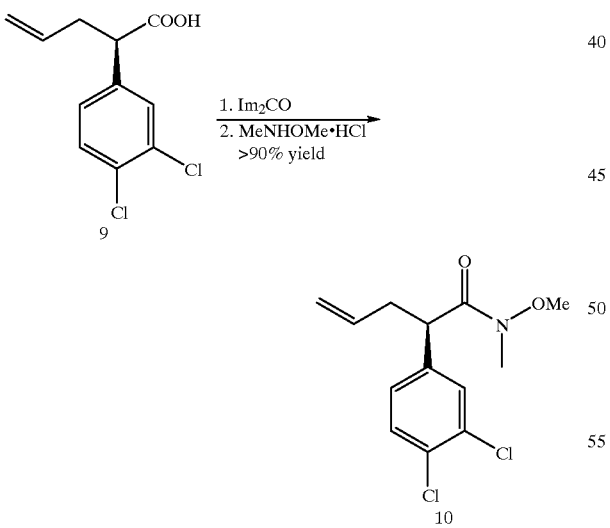

To a solution of acid 9 (10.9 g, 44.5 mmol) in 200 mL of CH₂Cl₂ at 0° C., Im₂CO (8.7 g, 53.5 mmol) was added. After stirring at 0° C. for 1 hour, MeNHOMe.HCl (10.8 g, 111.5 mmol) was added. The mixture was stirred at room temperature for 15 hours, and then was diluted with 100 mL of TBME. The organic solution was washed with 50 mL of 2N HCl, followed by 20% K₂CO₃ aqueous solution (50 mL), and was dried over MgSO₄. Removal of the solvent then gave the desired product 10 as an oil, with an enantiomeric ratio of 99:1, which was used without further purification.

¹H NMR (400 MHz, CDCl₃): δ 2.49 (m, 1H), 2.75 (m, 1H), 3.17 (s, 3H), 3.55 (s, 3H), 4.05 (br, 1H), 5.03 (m, 2H), 5.65 (m, 1H), 7.12–7.48 (m, 3H).

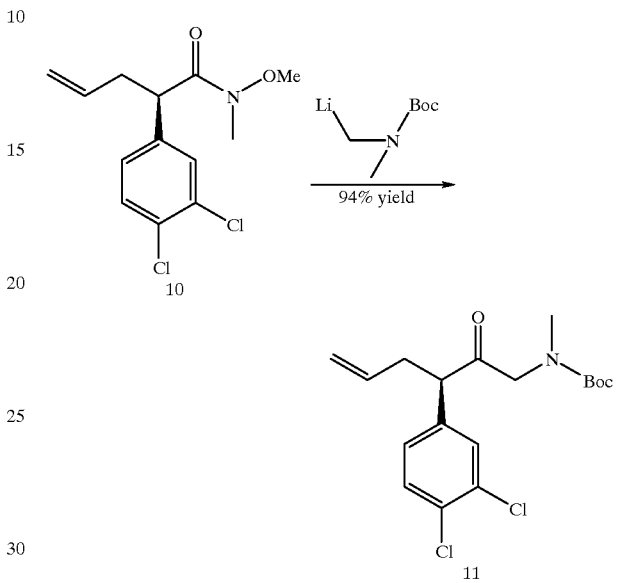

To a solution of N-Boc-dimethylamine (9.8 g, 67.8 mmol) in 120 mL of TBME, TMEDA (10 mL, 67.8 mmol) was added. The solution was cooled to −78° C., s-BuLi (1.3M in cyclohexane, 62.5 mL, 81.3 mmol) was added. The resulting mixture was stirred at −78° C. for 1 hour. A solution of amide 10 (7.8 g, 27.1 mmol) in 32 mL of THF was added. After stirring at −78° C. for 0.5 hours, the reaction was quenched by transfering into a solution of HOAc (24 mL) in 7 mL of MeOH and 200 mL of THF at −78° C. The organic solution was then washed with H₂O, aq. NaHCO₃ solution, and was dried over MgSO₄. Removal of solvents followed by column chromatography (silica gel, 30% TBME/heptane) gave the pure product 11 (9.5 g, 94% yield) as a colorless oil, with an enantiomeric ratio of 99:1.

¹H NMR (400 Mhz, CDCl₃): δ 1.34 (s, 9H), 2.35 (m, 1H), 2.75 (m, 1H), 2.78 (s, 3H), 3.72 (m, 1H), 3.83–4.10 (m, 2H), 4.97 (m, 2H), 5.58 (m, 1H), 7.02–7.41 (m, 3H).

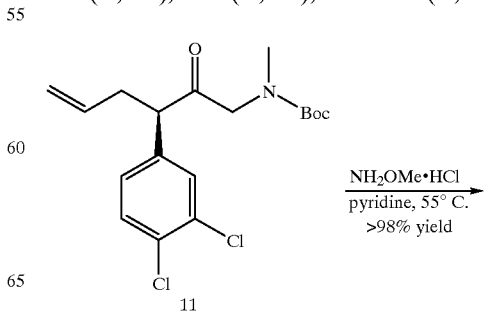

-continued

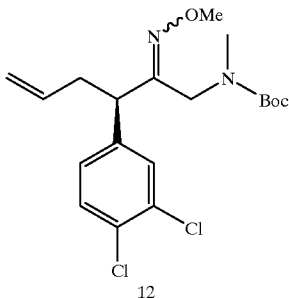
12

To a solution of ketone 11 (4.8 g, 12.9 mmol) in 20 mL of pyridine, NH$_2$OMe.HCl (2.5 g, 29.7 mmol) was added. The solution was heated to 50–55° C. for 7 hours. After cooling to room temperature, the reaction was diluted with 100 mL of TBME. The organic solution was washed with H$_2$O, aq. NaHCO$_3$ solution, and was dried over MgSO$_4$. Removal of solvents followed by column chromatography (silica gel, 10% TBME/heptane) gave 1.9 g of Z-oxime 12 and 3.2 g of E-oxime 12 (98% combined yield) as a colorless oil, with an enantiomeric ratio of greater than 98:2.

Z-isomer: $^1$H NMR (400 Mhz, CDCl$_3$): δ 1.48 (s, 9H), 2.35 (m, 1H), 2.50 (s, 3H), 2.70 (m, 1H), 3.49 (m, 1H), 3.83 (m, 1H), 3.94 (s, 3H), 4.25 (m, 1H), 4.97 (m, 2H), 5.68 (m, 1H), 7.08 (m, 1H), 7.31 (m, 2H).

E-isomer: $^1$H NMR (400 Mhz, CDCl$_3$): δ 1.35 (s, 9H), 2.35–2.67 (m, 5H), 3.69 (m, 1H), 3.85 (s, 3H), 4.15 (m, 1H), 4.42 (m, 1H), 5.05 (m, 2H), 5.68 (m 1H), 7.11 (m, 1H), 7.33 (m, 2H).

Compound 12 is a useful intermediate that can be used to prepare optically active compounds of formula (I) via the procedures set forth in steps 4 and 5, above.

EXAMPLE 3

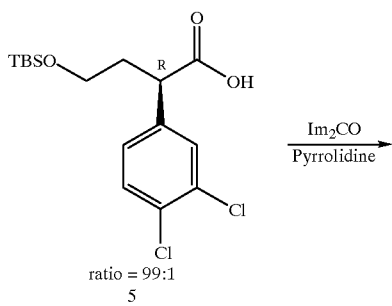
ratio = 99:1
5

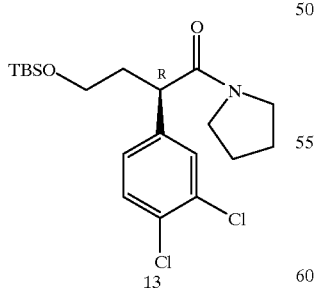
13

To a mixture of Im$_2$CO (9.6 g, 0.06 mol) in 100 mL of CH$_2$Cl$_2$ at 0° C., slowly add a solution of acid 5 (21.4 g, 0.059 mol), prepared as described in Example 1 above, in 100 mL of CH$_2$Cl$_2$. Stir the resulting solution at 0° C. for 1 hour. Add pyrrolidine (5.0 g, 0.071 mol). Stir the mixture at 0° C. for 6 hours, add 100 mL of 2N HCl, followed by 500 mL of heptane. Separate the organic layer, wash it with 20% K$_2$CO$_3$ aqueous solution (100 mL), and dry over MgSO$_4$. Remove the solvent to give the amide 13 as an oil, which may be used without further purification in the reaction below.

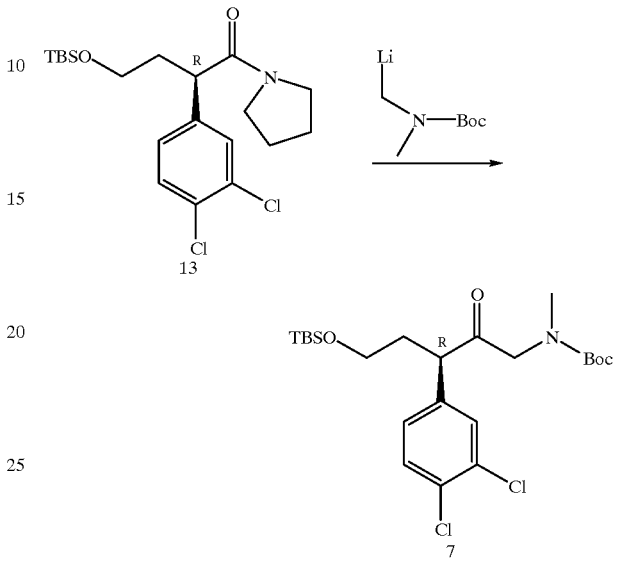

To a solution of N-Boc-dimethylamine (3.9 g, 26.7 mmol) in 50 mL of TBME, add TMEDA (4 mL, 26.7 mmol). Cool the solution to −78° C., and add s-BuLi (1.3M in cyclohexane, 24.7 mL, 32.1 mmol). Stir the resulting mixture at −78° C. for 1 hour. Add a solution of amide 13 (4.6 g, 10.7 mmol) in 15 mL of THF and stir at −78° C. for 0.5 hours. Quench the reaction by transfering into a solution of HOAc (15 mL) in 7 mL of MeOH and 20 mL of THF at −78° C. Wash the organic solution with H$_2$O, aq. NaHCO$_3$ solution, and dry over MgSO$_4$. Remove the solvents and subject to column chromatography (silica gel, 15% TBME/heptane) to give product 7 as a colorless oil.

Compound 7 is a useful intermediate that can be used to prepare optically active compounds of formula (I) via the procedures set forth in steps 3, 4 and 5, above.

We claim:

1. A process for making an optically active R-enantiomer compound having the formula:

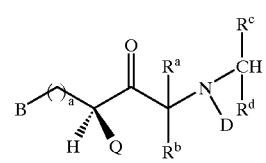

wherein B is —CH=CH$_2$, —CH$_2$OH, or —CH$_2$OR$^P$, and R$^P$ is an alcohol protecting group;

a is 1, 2, or 3;

Q is R$^5$-phenyl, R$^5$-naphthyl, or R$^5$-heteroaryl;

R$^5$ represents 1–3 substituents independently selected from the group consisting of H, halogeno, —OR$^6$, —OC(O)R$^6$, —OC(O)N(R$^6$) (R$^7$), —N(R$^6$)(R$^7$), C$_{1-6}$ alkyl, —CF$_3$, —C$_2$F$_5$, —COR$^6$, —CO$_2$R$^6$, —CON(R$^6$) (R$^7$), —S(O)$_e$R$^{13}$, —CN, —OCF$_3$, —NR$^6$CO$_2$R$^{16}$, —NR$^6$COR$^7$, —NR$^8$CON(R$^6$)(R$^7$), R$^{15}$-phenyl, R$^{15}$- benzyl, $NO_2$, $-N(R^6)S(O)_2R^{13}$ or $-S(O)_2N(R^6)(R^7)$; or adjacent $R^5$ substituents can form an $-O-CH_2-O-$ group;

$R^6$, $R^7$, $R^8$, and $R^{13}$ are independently selected from the group consisting of H, $C_{1-6}$ alkyl, $C_2-C_6$ hydroxyalkyl, $C_1-C_6$ alkoxy-$C_1-C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of $-O-$, $-S-$ and $-N(R^{19})-$;

$R^{15}$ is 1 to 3 substituents independently selected from the group consisting of H, $C_1-C_6$ alkyl, $C_1-C_6$ alkoxy, $C_1-C_6$ alkylthio, halogeno, $-CF_3$, $-C_2F_5$, $-COR^{10}$, $-CO_2R^{10}$, $-C(O)N(R^{10})_2$, $-S(O)_eR^{10a}$, $-CN$, $-N(R^{10})COR^{10}$, $-N(R^{10})CON(R^{10})_2$ and $-NO_2$;

$R^{16}$ is $C_{1-6}$ alkyl, $R^{15}$-phenyl or $R^{15}$-benzyl;

$R^{10}$ and $R^{10a}$ are independently selected from the group consisting of H and $C_{1-6}$ alkyl;

$R^{19}$ is H, $C_1-C_6$ alkyl, $-C(O)N(R^{10})_2$, $-CO_2R^{10}$, $-(C(R^8)(R^9))_f-CO_2R^{10}$ or $-(C(R^8)(R^9))_u-C(O)N(R^{10})_2$;

$R^9$ is selected from the group consisting of $R^6$ and $-OR^6$;

e is 0, 1 or 2, provided that when e is 1 or 2, $R^{13}$ and $R^{10a}$ are not H;

f is an integer from 1 to 6;

u is an integer from 0 to 6;

$R^a$ and $R^c$ are the same, and are H, or are selected from alkyl, cycloalkyl and aryl groups, said groups being optionally substituted with one or more substituents selected from alkyl, cycloalkyl, aryl, or $-OH$; or $R^a$ and $R^c$ together with the C—N—C chain to which they are bound, form a 5–7 membered ring;

$R^b$ and $R^d$ are the same, and are H, or are selected from alkyl, cycloalkyl and aryl groups, said groups being optionally substituted with one or more substituents selected from alkyl, cycloalkyl, aryl, or $-OH$; and D is a directing group capable of directing lithiation alpha to a nitrogen atom of a nitrogen compound having D as a substituent bound to the nitrogen atom when said nitrogen compound is reacted with s-butyl lithium, said nitrogen compound having the formula

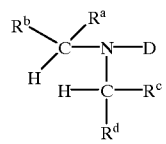

wherein $R^a$, $R^b$, $R^c$, and $R^d$ are as defined above;
said process comprising reacting a compound having the formula

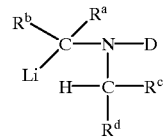

wherein $R^a$, $R^b$, $R^c$, and $R^d$ are as defined above, with a compound having the formula

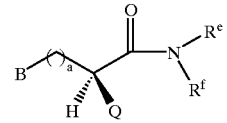

wherein B, a, $R^a$, $R^b$ and Q are as defined above, and $R^e$ and $R^f$ are independently selected from the group consisting of alkyl, alkoxy, cycloalkyl and aryl groups, said groups being optionally substituted with one or more substituents selected from alkyl, alkoxy, cycloalkyl, aryl, $NH_2$, or $-OH$, or $R^e$ and $R^f$ together with the nitrogen atom to which they are bound, form a 5–7 membered ring.

2. The process of claim 1 wherein $R^5$ represents 1–3 substituents selected from H and halogeno.

3. The process of claim 1 wherein $R^P$ is selected from the group consisting of silyl, alkyl, cycloalkyl, aryl, alkoxyalkyl, heterocycloalkyl, and heteroalkyl, optionally substituted with one or more alkyl, cycloalkyl, aryl, alkoxyalkyl, heterocycloalkyl, and heteroalkyl groups.

4. The process of claim 1, wherein D is $-C(O)R^A$, $-C(O)-N(R^A)(R^B)$, $-C(O)-OR^A$, $-CH=NR^A$, $-N=O$, $-C(=S)R^A$ or

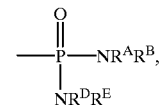

wherein $R^A$, $R^B$, $R^D$, and $R^E$ are independently selected from the group consisting of alkyl, aryl, and cycloalkyl, said groups being optionally substituted by one or more alkyl, aryl, or cycloalkyl groups.

5. The process of claim 1, wherein $R^P$ is selected from silyl, benzyl, tetrahydropyranyl, and alkoxymethyl and D is tert-butoxycarbonyl.

\* \* \* \* \*